United States Patent [19]

Young et al.

[11] 4,250,346
[45] Feb. 10, 1981

[54] LOW TEMPERATURE OXYDEHYDROGENATION OF ETHANE TO ETHYLENE

[75] Inventors: Frank G. Young; Erlind M. Thorsteinson, both of Charleston, W. Va.

[73] Assignee: Union Carbide Corporation, New York, N.Y.

[21] Appl. No.: 139,965

[22] Filed: Apr. 14, 1980

Related U.S. Application Data

[63] Continuation-in-part of Ser. No. 618,836, Oct. 1, 1975, abandoned.

[51] Int. Cl.³ .............................................. C07B 5/48
[52] U.S. Cl. ................................... 585/658; 252/462; 252/467
[58] Field of Search ................. 252/462, 467; 585/658

[56] References Cited

U.S. PATENT DOCUMENTS

| | | | |
|---|---|---|---|
| 2,487,563 | 11/1949 | Layng .................................. 260/668 |
| 3,222,417 | 12/1965 | Hughes ............................. 260/683.3 |
| 3,320,331 | 5/1967 | Gaspar et al. ..................... 260/683.3 |
| 3,356,757 | 12/1967 | Roth et al. ........................ 260/683.3 |
| 3,361,839 | 1/1968 | Lester .......................... 260/683.3 X |
| 3,600,443 | 8/1971 | Cevidalli et al. ............... 260/604 R |
| 3,636,156 | 1/1972 | Ozaki et al. ...................... 260/597 R |
| 3,678,124 | 7/1972 | Stepanov et al. ............. 260/683.3 X |
| 3,692,863 | 9/1972 | Kmecak et al. .................. 260/683.3 |
| 3,702,868 | 11/1972 | Santangelo et al. ............. 260/533 R |
| 3,725,246 | 4/1973 | Kmecak et al. .............. 260/683.3 X |
| 3,763,257 | 10/1973 | Bradshaw et al. ............ 260/683.3 X |
| 3,862,256 | 1/1975 | Isailingold et al. ........... 260/683.3 X |
| 3,887,495 | 6/1975 | Juguin et al. ................. 260/683.3 X |
| 3,887,631 | 6/1975 | Yaffe ................................. 260/680 E |
| 3,933,933 | 1/1976 | Bertus ........................... 260/683.3 X |
| 4,066,704 | 1/1978 | Harris et al. ...................... 260/604 R |

FOREIGN PATENT DOCUMENTS

| | | |
|---|---|---|
| 103438 | 3/1969 | Australia . |
| 103490 | 3/1969 | Australia . |
| 483190 | 4/1938 | United Kingdom . |
| 1377325 | 12/1974 | United Kingdom . |

Primary Examiner—Thomas A. Waltz
Attorney, Agent, or Firm—Gerald R. O'Brien, Jr.

[57] ABSTRACT

Ethane is catalytically oxydehydrogenated to ethylene in a gas phase reaction, in the presence or absence of water, at temperatures of $\leq 550°$ C. using a catalyst comprising oxides of the elements $$Mo_a X_b Y_c$$

wherein
X = Cr, Mn, Nb, Ta, Ti, V and/or W,
Y = Bi, Ce, Co, Cu, Fe, K, Mg, Ni, P, Pb, Sb, Si, Sn, Tl and/or U,
a = 1,
b = 0 to 2,
c = 0 to 2,
with the proviso that the total value of c for Co, Ni and and/or Fe is <0.5.

Acetic acid is also produced.

16 Claims, No Drawings

LOW TEMPERATURE OXYDEHYDROGENATION OF ETHANE TO ETHYLENE

This application is a continuation-in-part of our prior application Ser. No. 618,836 filed Oct. 1, 1975 and now abandoned, entitled "Low Temperature Oxydehydrogenation of Ethane to Ethylene."

BACKGROUND OF THE INVENTION

1. Field of the Invention

The invention relates to the gas phase catalytic dehydrogenation of ethane to ethylene in the presence of oxygen, i.e., the oxydehydrogenation of ethane to ethylene.

2. DESCRIPTION OF THE PRIOR ART

Ethylene has been conventionally prepared, commercially, by thermally cracking ethane in an endothermic reaction which is carried out at temperatures of about 600° to 1000° C. (U.S. Pat. No. 3,541,179). The reaction time in such process is very short, which makes it difficult or impossible to efficiently recover heat from the process stream. Further, the high temperatures which are used require the use of special alloys in the construction of the furnaces or the reaction vessels in which the reaction is conducted. The cracking reaction also causes the formation of relatively large amounts of low boiling by-products such as hydrogen and methane which complicates, and makes more expensive, the recovery of the ethylene from such by-products.

It is possible to oxydehydrogenate ethane by using a variety of oxyhalogenation catalyst systems in an exothermic reaction. These reactions, however, have only been accomplished at temperatures of at least about 500° to 600° C. (U.S. Pat. No. 3,080,435). Furthermore, the presence of the halogen atoms increases the difficulty of recovering any olefins which are produced. Also, exotic and expensive materials of construction are required to withstand corrosion by the halogens and hydrogen halides in the reaction systems. Further, the halogens themselves must be recovered and recycled to make the system economical.

The oxydehydrogenation of selected $\geq C_3$ alkanes, at relatively high temperatures in an exothermic reaction has also been accomplished with selected catalysts which contain vanadium (U.S. Pat. Nos. 3,218,368, 3,541,179 and 3,856,881) and vanadium and molybdenum (U.S. Pat. No. 3,320,331).

The use of molybdenum and vanadium containing catalyst systems for the gas phase oxidation of alpha-beta unsaturated aliphatic aldehydes, such as acrolein, to the corresponding alpha, beta unsaturated carboxylic acids, such as acrylic acid, has been known. These catalyst systems include those containing the elements Mo, V and X, where X is Nb, Ti or Ta as disclosed in Belgian Pat. Nos. 831,322; 821,324 and 821,325.

Prior to the present invention, however, it has not been possible to readily oxydehydrogenate ethane to ethylene at relatively low temperatures with relatively high levels of conversion, selectivity and productivity.

The terms percent conversion, percent selectivity and productivity which are employed herein with respect to the present invention are defined as follows:

$$\% \text{ conversion (of ethane)} = 100 \times \frac{A}{\text{moles of ethane in the reaction mixture which is fed to the catalyst bed}} \quad \text{I}$$

wherein $A$ = the molar ethane-equivalent sum (carbon basis) of all carbon-containing products, excluding the ethane in the effluent  Ia $$\% \text{ selectivity (or efficiency) for ethylene (or acetic acid)} = 100 \times \frac{\text{moles of ethylene (or acetic acid) produced}}{A} \quad \text{II}$$

productivity for ethylene (or acetic acid) = pounds of ethylene (or acetic acid) produced per cubic foot of catalyst (in the catalyst bed) per hour of reaction time.  III

SUMMARY OF THE INVENTION

Ethane is oxydehydrogenated to ethylene in a gas phase reaction at relatively high levels of conversion, selectivity and productivity and at temperatures of less than about 550° C. and preferably of less than 450° C., with certain catalyst compositions containing molybdenum and various other optional elements.

An object of the present invention is to provide a process whereby ethane can be oxydehydrogenated to ethylene at relatively low temperatures with relatively high levels of conversion, selectivity and productivity.

A further object of the present invention is to provide a process whereby ethane can be oxydehydrogenated in the presence of water at relatively low temperatures to produce relatively high levels of conversion, selectivity and productivity with respect to the products ethylene and acetic acid.

A further object of the present invention is to provide a process whereby ethane can be oxydehydrogenated to ethylene without the concurrent production of significant amounts of gaseous by-products such as methane and hydrogen that would render the cryogenic separation and purification of the ethylene difficult and costly.

A further object of the present invention is to provide novel catalyst compositions for the vapor phase oxydehydrogenation of ethane to ethylene at relatively low temperatures.

These and other objects of the present invention are achieved by using as a catalyst, in the exothermic vapor phase oxydehydrogenation of ethane, a composition comprising the elements Mo, X and Y in the ratio $$Mo_a X_b Y_c$$

X is Cr, Mn, Nb, Ta, Ti, V and/or W, and preferably Mn, Nb, V and/or W,

Y is Bi, Ce, Co, Cu, Fe, K, Mg, Ni, P, Pb, Sb, Si, Sn, Tl and/or U, and preferably Sb, Ce, and/or U.

a is 1, b is 0.05 to 1.0, and c is 0 to 2, and preferably 0.05 to 1.0, with the proviso that the total value of c for Co, Ni and/or Fe is <0.5.

The numerical values of a, b, and c represent the relative gram-atom ratios of the elements Mo, X and Y, respectively, which are present in the catalyst composition.

The Si used in forming the catalyst composition shown above is other than that which may be present in any support on which the catalyst may be employed, as disclosed below.

The Catalyst

The elements Mo, X and Y are present in the catalyst composition in combination with oxygen in the form, it is believed of various oxides, as such, and possibly as chemical combinations of oxides such as spinels and perovskites.

The catalyst is preferably prepared from a solution of soluble compounds (salts, complexes or other compounds) of each of the elements Mo, X and Y or, in the case of Si and Sb, also a colloidal sol. The solution is preferably an aqueous system having a pH of 1 to 7, and preferably 2 to 6. The solution of the element containing compounds is prepared by dissolving sufficient quantities of soluble compounds of each of the elements, so as to provide the desired a:b:c gram-atom ratios of the elements Mo, X and Y, respectively. To the extent possible the selected compounds of the various elements should be mutually soluble. The Si compounds are usually added in the form of a colloidal silica sol. Where any of the selected compounds of such elements, other than Si, are not mutually soluble with the other compounds, they can be added last to the solution system. The catalyst composition is then prepared by removing the water or other solvent from the mixture of the compounds in the solution system.

The water or other solvent can be removed by evaporation from the mixture resulting from the combination of all the compounds and solvents.

Where the catalyst is to be used on a support, the compounds of the desired elements are deposited on a particulate porous support usually having the following physical properties, but not limited to these: a surface area of about 0.1 to 500 square meters per gram; an apparent porosity of 30 to 60%; with at least 90% of the pores having a pore diameter in the range of 20-1500 microns; and the form of the particles or pellets being about ⅛ to 5/16 inch in diameter. The deposition is accomplished by immersing the support in the ultimate mixture of all the compounds, evaporating off the major portion of the solvent, and then drying the system at about 80° to 220° C. for 2 to 60 hours. The dried catalyst is then calcined by being heated at about 220° to 550° C. in air or oxygen for ½ to 24 hours to produce the desired $Mo_aX_bY_c$ composition.

The supports which may be used include silica, aluminum oxide, silicon carbide, zirconia, titania and mixtures thereof.

When used on a support, the supported catalyst usually comprises about 10 to 50 weight % of the catalyst composition, with the remainder being the support.

The molybdenum is preferably introduced into solution in the form of ammonium salts thereof such as ammonium paramolybdate, and organic acid salts of molybdenum such as acetates, oxalates, mandelates and glycolates. Other water soluble molybdenum compounds which may be used are partially water soluble molybdenum oxides, molybdic acid, and the chlorides of molybdenum.

The vanadium, when used, is preferably introduced into solution in the form of ammonium salts thereof such as ammonium meta-vanadate and ammonium decavanadate, and organic acid salts of vanadium such as acetates, oxalates and tartrates. Other water soluble vanadium compounds which may be used are partially water soluble vanadium oxides, and the sulfates of vanadium.

The niobium and tantalum, when used, are preferably introduced into solution in the form of oxalates. Other sources of these metals in soluble form, which may be used are compounds in which the metal is coordinated, bonded, or complexed to a beta-diketonate, a carboxylic acid, an amine, an alcohol or an alkanolamine.

The titanium, when used, is preferably introduced into solution in the form of a water soluble chelate coordinated with ammonium lactate. Other soluble titanium compounds which may be used are those in which titanium is coordinated, bonded, or complexed to a beta-diketonate, a carboxylic acid, an amine, an alcohol or an alkanolamine.

The iron, nickel, cobalt, manganese, copper, chromium, bismuth, uranium, cerium, potassium, thallium, magnesium and lead, when used, are preferably introduced into solution in the form of nitrates. Other water soluble compounds of these elements which may be used are the water soluble chlorides and organic acid salts such as acetates, oxalates, tartrates, lactates, salicylates, formates and carbonates of such elements.

The antimony and tin, when used, are preferably introduced into the catalyst system in the form of water insoluble oxides. Water soluble compounds of these elements which may be used are antimony trichloride, stannic chloride, stannous chloride, stannic sulfate and stannous sulfate. Other water insoluble compounds of these elements which may be used are stannous hydroxide and stannous oxalate.

The tungsten, when used, is preferably introduced into solution in the form of ammonium salts such as ammonium paratungstate. Other water soluble tungsten compounds which may be used are the tungstic acids.

When silicon is used it is preferably introduced into the catalyst system in the form of an aqueous colloidal silica ($SiO_2$) sol.

When phosphorus is used it is preferably introduced into the catalyst system as phosphoric acid or as a water soluble phosphate.

It is believed that, for the catalysts to be most effective, the Mo, X and Y metal components should be slightly reduced below their highest possible oxidation states. This may be accomplished during the thermal treatment of the catalyst in the presence of reducing agents such as $NH_3$ or organic reducing agents, such as the organic complexing agents, which are introduced into the solution systems from which the catalysts are prepared. The catalyst may also be reduced in the reactors in which the oxidation reaction is to be conducted by the passage of hydrogen or hydrocarbon reducing agents such as ethane, ethylene, or propylene through the catalyst bed.

The catalysts, supported or unsupported can be used in a fixed or fluidized bed.

The Ethane

The raw material which is used as the source of the ethane should be a gas stream which contains, at atmospheric pressure, at least 3 volume percent of ethane. It may also contain minor amounts, i.e., <5 volume percent, of each of $H_2$, CO and the $C_3$-$C_4$ alkanes and alkenes. It may also contain major amounts, i.e., >5 volume percent of $N_2$, $CH_4$, $CO_2$ and water, as steam.

The catalysts of the present invention appear to be specific with respect to their ability to oxydehydrogenate ethane to ethylene, since the catalysts do not oxydehydrogenate propane, n-butane and butene-1, but rather burn these materials to carbon dioxide, and other oxidized carbonaceous products.

The Reaction Mixture

The components of the gaseous reaction mixture which is used as the feed stream in the process of the present invention and the relative ratios of the components in such mixture are the following:

one mole of ethane, 0.01 to ½ mole of molecular oxygen (as pure oxygen or in the form of air), and 0 to 0.4 mole of water (in the form of steam).

The water or steam is used as reaction diluent and as a heat moderator for the reaction. Other materials which may be used as reaction diluents or heat moderators are such inert gases as nitrogen, helium, $CO_2$, and methane.

During the normal course of the reaction, in the absence of added water, one mol of water is formed per mol of ethane that is oxydehydrogenated. This water that is generated during the reaction will, in turn, cause the formation of some acetic acid, i.e., about 0.05 to 0.25 mols, per mol of ethylene that is formed. The water that is added to the feed stream will cause the formation of additional amounts of acetic acid, i.e., up to about 0.25 to 0.95 mols of acetic acid per mol of ethylene that is formed.

The components of the reaction mixture are uniformly admixed prior to being introduced into the reaction zone. The components are preheated, individually or after being admixed, prior to their being introduced into the reaction zone, to a temperature of about 200° to 500° C.

Reaction Conditions

The preheated reaction mixture is brought into contact with the catalyst composition, in the reaction zone, under the following conditions:

pressure of about 1 to 30, and preferably of about 1 to 20, atmospheres, temperature of about 150° to 550° C., and preferably, of about 200° to 400° C., contact time (reaction mixture on catalyst) of about 0.1 to 100, and preferably of about 1 to 10, seconds, and, space velocity of about 50 to 5000 $h^{-1}$, preferably 200 to to 3000 $h^{-1}$.

The contact time may also be defined as the ratio between the apparent volume of the catalyst bed and the volume of the gaseous reaction mixture fed to the catalyst bed under the given reaction conditions in a unit of time.

The reaction pressure is initially provided by the feed of gaseous reactants and diluents, and after the reaction is commenced, the pressure may be maintained, preferably, by the use of suitable back-pressure controllers placed on the gaseous effluent side of the catalyst bed.

The reaction temperature is preferably provided by placing the catalyst bed within a tubular converter whose walls are immersed in a suitable heat transfer medium, such as tetralin, molten salt mixtures, or other suitable heat transfer agent, which is heated to the desired reaction temperature.

The process of the present invention can be used without added diluents, other than water, to selectively oxydehydrogenate ethane to ethylene and acetic acid to provide % conversion, % efficiencies and productivities, relative to those end products, of the order of

| End Product | (Ethane) % Conversion | % Efficiency | Productivity |
|---|---|---|---|
| Ethylene (without added $H_2$)* | 2 to 7 | 60–85 | 4 to 7.5 |
| Ethylene (with added $H_2O$)* | 2 to 8 | 50–80 | 2 to 8.5 |
| Acetic Acid (without added $H_2O$)* | 2 to 7 | 15–25 | 1.5 to 4 |
| Acetic Acid (with added $H_2O$)* | 2 to 8 | 15–45 | 2.5 to 5 |

*i.e. with or without $H_2O$ added to the ethane feed gas

The preferred catalysts for achieving the highest conversion and efficiencies relative to ethylene and acetic acid are those calcined compositions containing the elements Mo, V, Nb and Mn in the ratio $Mo_dV_eNb_fMn_g$ in which:

$d = 16$, $e = 1$ to 8, $f = 0.2$ to 10, $g = 0.1$ to 5.

Another preferred catalyst group for operation at a temperature up to 450° C. is the calcined compositions containing the elements Mo, X and Y in the ratio:

$$Mo_aX_bY_c$$

wherein X is selected from the elements Ta, Ti, V and Mn; Y is selected from the group comprising the elements Fe, Sb, Si and Sn;

a is 1 b is 0.05 to 1.0 c is 0.05 to 1.0, with the proviso that the total value of c for Fe is less than 0.5.

The following examples are merely illustrative of the present invention and are not intended as a limitation upon the scope thereof.

The examples provided below disclose the preparation of various catalyst compositions, and the use of such compositions in the oxydehydrogenation of ethane to ethylene.

The activity of each experimental catalyst was determined in either a microscale U shaped tubular reactor into which a pulsed flow of oxygen and ethane were fed (Test Procedure A); or in a straight tubular reactor in which the ethane and oxygen were concurrently fed continuously (Test Procedure B); or in a back-mix autoclave process (Test Procedure C). These test procedures are described in more detail below.

Catalyst Test Procedure A

Catalysts were screened for activity for the (oxy) dehydrogenation of ethane in a pulse microreactor system. The reaction section, a 20" long by 8 mm diameter silica U-tube, holding the catalyst under test was heated by immersion in a fluidized sand-bath, whose temperature was controlled by a thermocouple controller. The thermocouples for temperature control and measurement were immersed in the fluidized sand, which extended at least three inches above the level of the catalyst in the U-tube. Preliminary exploration of the temperature profile in the sand-bath showed less than a 3-degree variation from top to bottom from the fixed-point set by the controller.

The microreactor was close-coupled to a gas chromatograph for analysis of the product streams. The helium carrier supply flowing through the microreactor was taken from the chromatograph by interrupting the helium-supply line inside the chromatograph at a point directly after the flow-controller, leading it through an 8-port, 2-position valve, [Union Carbide Corporation, Special Instruments Division, Model C4-70], and thence through a 6-port manual sample injection valve ]Union Carbide Model 2112-50-2], to the inlet leg of the U-tube reactor. The system was equipped with an injection port holding a rubber septum at the reactor inlet. Product gas from the reactor was led through a cold-trap, back through the 8-port valve, which served to switch the product stream to either of the two analysis systems of the chromatograph. Each valve was equipped with an adjustable by-pass valve to equalize the pressure-drop of the chromatograph column in its analysis system.

Injection of 2.0 ml pulses of feed gas, composition: (% by volume) oxygen 6.5%, ethane 8.0%, balance nitrogen, was made by gas-tight syringe, through the port directly ahead of the catalyst. The gas was diluted and carried over the catalyst, 3.0 grams, by the helium carrier gas, which passed at all times through the reactor at 60 ml/min and through the gaschromatrograph for analysis.

Analysis of the product mixture was made on a $10' \times \frac{1}{8}''$ dia. stainless steel column packed with Poropak (T.M.) R. The column was heated at 10° C./minute, starting at 30° C. Under these conditions the retention times were: air, 2.0 min.; carbon dioxide, 2.5 min.; ethylene, b 3.4 min.; ethane, 4.0 min. The identity of the products was confirmed by chromatography of known pure samples, and by subjecting the separated peaks to mass spectrometric examination. Poropak R is a particulate, spherical shaped polystyrene resin cross-linked with divinyl benzene.

Catalyst Test Procedure B

The catalysts were tested in a tubular reactor under the following conditions: ethane gas feed composition (% by volume), 9.0% $C_2H_6$, 6.0% $O_2$, and 85% $N_2$; space velocity of 340 $hr^{-1}$; 1 atm total reaction pressure. As the temperature was raised, the catalyst activity was noted. The reactor consisted of a $\frac{1}{2}''$ stainless steel, straight tube heated by means of a molten salt bath (using DuPont HITEC (T.M.) heat transfer salt) of approximately 12" depth. A $\frac{1}{8}''$ thermocouple sleeve ran the entire length of the center of reactor tube and catalyst bed. The catalyst temperature profile could be obtained by sliding the thermocouple through the sleeve. Twenty-six ml of catalyst were introduced into the tube so that the top of the catalyst bed was 4" below the surface of the heat transfer salt. The catalyst bed was 5-5½" in length so that it had a depth cross-section ratio >10. The zone above the catalyst bed was filled with glass beads to serve as a preheater. The gaseous effluent from the reactor was passed through a condenser and trap at 0°. The gas and liquid products thus obtained were analyzed as described below.

Catalyst Test Procedure C

The reactor used in this high pressure study was a bottom-agitated "Magnedrive" autoclave with a centrally positioned catalyst basket and a side product effluent line. A variable speed, magnetically driven fan continuously recirculated the reaction mixture over the catalyst bed. The reactor is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty-fourth National Meeting of the American Institute of Chemical Engineers (AIChE), at New Orleans, Louisiana, on Mar. 16–20, 1969 and obtainable from AIChE at 345 East 47th Street, New York, New York 10017, which disclosure is incorporated herein by reference.

The back mix autoclave has a catalyst container made of stainless steel positions above the blades of the agitator fan. Thus, the fan blows the gas upward and inward in a convectional manner through the catalyst bed. Two thermocouples measure the inlet and outlet gas temperatures. Oxygen was fed through a rotameter at about 150 psig into the reactor through a $\frac{1}{4}''$ line. The gaseous, ethane-$CO_x$ mixtures were fed through a rotometer and then joined with the oxygen feed before being introduced into the reactor. The liquids were pumped directly into the reactor through the same feed line as the gases, but the liquids inlet joined the line after the gases were mixed. Effluent gases were removed through a port in the side of the reactor. Condensable liquid products were removed by a series of cold traps in two baths. The first bath contained wet ice at 0° C. and had two cold traps immersed in it. The second bath, of dry ice and acetone at −78° C., contained two cold traps. The non-condensable components of the exit stream were vented through a dry gas-test meter at atmospheric pressure to determine their total volume. An eight port sampling valve permitted the direct sampling of both product and feed gases through lines connected directly to the reactor feed and product streams. No external recycling was employed.

The bulk volume of the weighed catalyst sample was determined (about 150 cc.), and the sample was placed in the catalyst basket. The quantity of catalyst charged in each case was about 131.1 gms. Stainless steel screens were placed above and below the catalyst bed to minimize catalyst attrition and circulation of catalyst fine particles. After the catalyst basket was charged to the reactor, and the reactor sealed, the process lines were pressure tested at ambient temperatures to a pressure about 100 to 200 psig in excess of the maximum anticipated working pressure. Nitrogen was used for this test.

When the reactor was shown to be leak free, pure $N_2$ was passed through the reactor, and the temperature was raised between 275° C. and 325° C. The gas feed composition was varied in the range, (% by volume), 76% to 97% $C_2H_6$, 3% to 6% $O_2$, 0% to 10% $H_2O$, and 0% to 10% $CO_x$. After the desired temperature was attained, the oxygen and ethane-$CO_x$ mixtures were adjusted to give the desired steady state ratio at the desired overall flow rate. The concentrations of the components in the effluent gas were determined by the gas chromatographic analysis described below. A period of about 0.5 to one hour was allowed for the reactor to reach a steady state at the desired temperature. The liquid product traps were then drained, a dry gas test meter reading was taken, and the time was noted as the beginning of a run. During the course of a run, the effluent gas samples were analyzed for $C_2H_6$, $C_2H_4$, $O_2$, CO, $CO_2$, and other volatile hydrocarbons. At the end of a run, the liquid product was collected, and the volume of effluent gas was noted. The liquid products were analyzed by mass spectroscopy.

The reactor inlet and outlet gases from all of the tests conducted under Test Procedures B and C were analyzed for $O_2$, $N_2$ and CO on a $10' \times \frac{1}{8}''$ column of 5A molecular sieves (14/30-mesh) at 95° C., and for (O₂, N₂, CO together), CO₂, ethylene, ethane, and H₂O on a 14'×⅛" column of Poropak Q (80/100-mesh) at 95° C. The liquid product (when enough was obtained) was analyzed for H₂O, acetaldehyde, acetic acid, and other components by mass spectroscopy. Poropak Q (T.M.) is a particulate, spherical shaped polystyrene resin cross-linked with divinyl benzene.

In all cases % conversion and % selectivity were based on the stoichiometry:

$$C_2H_6 + \tfrac{1}{2}O_2 \rightarrow C_2H_4 + H_2O$$

$$C_2H_6 + 7/2 O_2 \rightarrow 2CO_2 + 3H_2O$$

without applying individual response factors to the eluted peak areas of the chromatograms.

The reaction condition of the three test procedures were as follows:

| Catalyst Test Procedure | Pressure Atmospheres | Temp., °C. | Contact Time, Seconds | Space Velocity h⁻¹ |
|---|---|---|---|---|
| A | 3.3 | 200 to 650 | — | — |
| B | 1 | 300–400 | 10.6 | 340 |
| C | 6–10 | 275–325 | 10.0/75psi 15.6/125psi | 2200 |

EXAMPLES 1-23

Catalysts 1–22 were prepared as disclosed below, and evaluated in Catalyst test Procedure A. The composition of each catalyst is given at the heading of the respective examples, and the test results are given in Table I below. The catalyst of Example 23 was evaluated in test Procedure B, and these test results are also shown in Table I.

In testing the catalysts of Examples 1–23, each catalyst was first tested to find the lowest temperature at which catalytic activity was first provided by the catalyst. This was designated as the temperature of Initial Activity (To). The selectivity of the catalyst for oxygehydrogenating ethane to ethylene at such To was then determined. Each active catalyst was then evaluated at higher temperatures to determine the lowest temperature, above To, at which a 10% conversion of ethane to ethylene could be achieved, and this temperature is reporte in Table I as $T_{10}$. The selectivity of the catalyst for oxydehydrogenative ethane to ethylene at $T_{10}$ was also determined and reported in Table I.

EXAMPLE 1

$Mo_1$

Two hundred fifty (250) grams of molybdenum trioxide (99.95% pure) was mixed with 7.8 grams of Carbowax 6M, a polyethyleneoxide wax; and pelleted into 5/16" diameter cylinders, 0.2490" long and having an axial hole 3/32" in diameter. The pellets were roasted at 750° C. for 3 hours to produce an unsupported catalyst.

EXAMPLE 2

$Mo_{16}Mn_{16}$ or $Mo_1Mn_1$

Eighty-eight point twenty-eight (88.28) grams of ammonium paramolybdate (0.5 gram atoms of Mo) were added to 177.89 grams of a 50.3 percent solution of manganous nitrate (0.5 gram atoms Mn) dissolved in 500 ml water.

The resulting mixture was heated to 80°–90° C. while stirring and 14% aq. ammonia was added to give a pH of 5. This was followed by drying by evaporation with stirring on a steam bath. Further drying was carried out at a temperature of 110° for a period of 16 hours.

The dried material was then transferred to a silica dish and calcined in a muffle furnace for 2 hours at 520° in an ambient atmosphere of air. The amount of unsupported catalyst obtained is 107 grams.

EXAMPLE 3

$Mo_{16}Nb_4$ or $Mo_1Nb_{0.25}$

Forty-two point four (42.4) grams of ammonium paramolybdate (0.24 gram atoms of Mo) were dissolved in 200 milliliters of water while stirring at 60°–80°, in a stainless steel evaporating dish.

To the resulting solution was added 74 ml of niobium oxalate solution (containing 183.9 gm/l) (0.06 gram atoms Nb).

The resulting mixture was heated while stirring and 87 grams (100 ml) Norton silica-alumina SA5205 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catatlyst deposited on the support calculated from the weight increase of the catalyst obtained is 31.5%.

EXAMPLE 4

$Mo_{16}Ti_4$ or $Mo_1Ti_{0.25}$

Four-hundred ninety-five (495) grams of ammonium paramolybdate (2.8 gram atoms of Mo) were dissolved in 1 liter of water while stirring at 60°–80°, in a stainless steel avaporating dish.

To the resulting solution were added 408 grams of Titanium lactate solution, "TYZOR LA" (0.7 gram atoms Ti).

The resulting mixture was heated while stirring and 1040 grams (1000 ml) Norton silica-alumina SA5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 21.2%.

EXAMPLE 5

$Mo_{16}V_{1.4}(\theta\text{-phase})$ or $Mo_1V_{0.088}$

Two hundred seventy-three point five (273.5) grams (1.9 g atoms Mo) of molybdenum trioxide, 51.2 grams (0.4 g atoms Mo) of 94 percent molybdenum dioxide, and 18.2 grams (0.1 g atoms) of vanadium pentoxide were ground together on a ball mill for 24 hours. The powder was sealed in a silica tube and heated at 700° C. for 90 hours. After cooling the unsupported product had a surface area of 2.36 m²/gm, a density of 4.01 gm/cc, and a porosity of 0.076 cc/gm. X-ray diffraction showed that it was the pure $\theta$-phase, $(V_{0.08}Mo_{0.92})_5O_{14}$.

EXAMPLE 6

$Mo_{16}V_4$ or $Mo_1V_{0.25}$

Eighty-two (82) grams of ammonium meta-vanadate (0.7 gram atoms of V) and 495 grams of ammonium paramolybdate (2.8 gram atoms of Mo) were dissolved in 2 liters of water while stirring at 60°–80°, in a stainless steel evaporating dish.

The resulting mixture was heated while stirring and 1040 grams (1000 ml) Norton silica-allumina SA5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 26.45%.

EXAMPLE 7

$Mo_{16}W_{5.3}$ or $Mo_1W_{0.33}$

Two-hundred nine (209) grams of ammonium tungstate (0.8 gram atoms of W) and 424 grams of ammonium paramolybdate (2.4 gram atoms of Mo) were dissolved in 4 liters of water while stirring at 60°–80°, in a stainless steel evaporating dish.

To the resulting solution were added 142 grams of ammonium oxalate (1.0 gram molecule) and 28 grams of nitric acid dissolved in 100 ml water.

The resulting mixture was heated while stirring and 1040 grams (1000 ml) Norton silica-alumina SA5218 ¼" spheres were added. This was followed by drying by evaporation with stirring on a steam bath. Further drying was carried out at a temperature of 120° for a period of 16 hours.

The dried material was then transferred to a tray fabricated from 1-mesh stainless steel wire screen and calcined in a muffle furnace for 8 hours at 350° in an ambient atmosphere of air. The amount of catalyst deposited on the support calculated from the weight increase of the catalyst obtained is 21.6%.

EXAMPLE 8

$Mo_{16}V_4Fe_1$ or $Mo_1V_{0.25}Fe_{0.0625}$

Seventy (70) grams of ammonium meta-vanadate (0.6 gram atoms of V) and 424 grams of ammonium paramolybdate (2.4 gram atoms of Mo) were dissolved in 2 liters of water while stirring at 60°–80°, in a stainless steel evaporating dish.

To the resulting solution was added 60 grams of ferric nitrate nonahydrate (0.15 gram atoms iron) dissolved in 100 ml water.

The resulting mixture was heated while stirring and 1040 grams (1000 ml) Norton silica-alumina SA5218 ¼" spheres were added. This was followed by drying by evaporation with stirring on a steam bath. Further drying was carried out at a temperature of 120° for a period of 16 hours.

The dried material was then transferred to a tray fabricated from 1-mesh stainless steel wire screen and calcined in a muffle furnace for 5 hours at 400° in an ambient atmosphere of air. The amount of catalyst deposited on the support calculated from the weight increase of the catalyst obtained is 27.5%.

EXAMPLE 9

$Mo_{16}V_4Mn_4$ or $Mo_1V_{0.25}Mn_{0.25}$

Thirty-five (35) grams of ammonium metavanadate (0.3 gram atoms of V) and 212 grams of ammonium paramolybdate (1.2 gram atoms of Mo) were dissolved in 1 liter of water while stirring at 60°–80°, in a stainless steel evaporating dish.

To the resulting solution were added 75 grams of manganous acetate tetrahydrate (0.3 gram atoms Mn) dissolved in 100 ml water.

The resulting mixture was heated while stirring. This was followed by drying by evaporation with stirring on a steam bath. Further drying was carried out at a temperature of 120° for a period of 40 hours.

The dried material was then transferred to a silica dish and calcined in a muffle furnace for 5 hours at 400° in an ambient atmosphere of air. The amount of unsupported catalyst obtained is 222 grams.

EXAMPLE 10

$Mo_{16}V_4Nb_2$ or $Mo_1V_{0.25}Nb_{0.125}$

Eighty-two (82) grams of ammonium meta-vanadate (0.7 gram atoms of V) and 494 grams of ammonium paramolybdate (2.8 gram atoms of Mo) were dissolved in 2 liters of water while stirring at 60°–80°, in a stainless steel evaporating dish.

To the resulting solution were added 550 grams of niobium oxalate sol (0.35 gram atoms Nb) and 28 grams of ammonium nitrate dissolved in 100 ml water.

The resulting mixture was heated while stirring and 1040 grams (1000 ml) Norton silica-alumina SA5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.7%.

The niobium oxalate sol, containing the equivalent of 95.3 gm/l of $Nb_2O_5$ is a product of Kawecki Berylco Industries.

EXAMPLE 11

$Mo_{16}W_2Nb_4$ or $Mo_1W_{0.125}Nb_{0.25}$

Seven point eight (7.8) grams of ammonium paratungstate (0.03 gram atoms of W) and 42.4 grams of ammonium paramolybdate (0.24 gram atoms of Mo) were dissolved in 400 ml of water while stirring at 60°–80°, in a stainless steel evaporating dish.

To the resulting solution were added 74 ml of a solution of niobium oxalate containing 183.9 grams/l (0.06 gram atoms Nb).

The resulting mixture was heated while stirring and 87 grams (100 ml) Norton silica-alumina SA5205 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 55.2%.

EXAMPLE 12

$Mo_{16}W_{3.3}Pb_{1.9}$ or $Mo_1W_{0.2}Pb_{0.12}$

One hundred seventy-seven (177) grams of ammonium para-tungstate (0.679 gram atoms of V) and 369 grams of ammonium para-molybdate (2.087 gram atoms of Mo) were dissolved in 2 liters of water while stirring at 60°–80°, in a stainless steel evaporating dish.

To the resulting solution were added 83 grams of lead nitrate (0.252 gram atoms Pb) and 20 ml of nitric acid dissolved in 450 ml water.

The resulting mixture was heated while stirring and 770 grams (1000 ml) Norton silica-alumina SA5205 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 37.2%.

EXAMPLE 13

$Mo_{16}Nb_4W_{1.6}Mn_4$ or $Mo_1Nb_{0.25}W_{0.1}Mn_{0.25}$

Three thousand three hundred forty-eight (3348) ml of niobium oxalate solution, containing 319.1 grams $Nb_2O_5$ (2.4 gram atoms of Nb) and 1696 grams of ammonium paramolybdate (9.6 gram atoms of Mo) were dissolved in 4 liters of water while stirring at 60°–80°, in a stainless steel evaporating dish.

To the resulting solution were added 240 grams of ammonium paratungstate (0.92 gram atoms tungsten) and 880 grams of 50.3 percent solution of manganous nitrate (2.46 gram atoms manganese) dissolved in 4000 ml water.

The resulting mixture was heated while stirring and evaporated to a paste. This was transferred to furnace trays and dried in a circulatory air current at 80°–90° C. overnight. Further drying was carried out at a temperature of 120° for a period of 64 hours.

The dried material was then transferred to a tray fabricated from 10-mesh stainless steel wire screen and calcined in a muffle furnace for 5 hours at 360° in an ambient atmosphere of nitrogen. The amount of unsupported catalyst is 2027 grams. The catalyst was reduced to 25-mesh.

EXAMPLE 14

$Mo_{16}V_4Nb_1Mn_1$ or $Mo_1V_{0.25}Nb_{0.0625}Mn_{0.0625}$

Two-hundred ten (210) grams of ammonium metavanadate (1.8 gram atoms of V) and 1272 grams of ammonium paramolybdate (7.2 gram atoms of Mo) were dissolved in 5.5 liters of water while stirring at 60°–80°, in a stainless steel evaporating dish.

To the resulting solution were added 416 grams of niobium oxalate sol (0.45 gram atoms Nb) and 160 grams of manganous nitrate (50.3% solution), (0.45 gram atoms Mn) dissolved in 150 ml water.

The resulting mixture was heated while stirring and 3120 grams (3000 ml) Norton silica-alumina SA5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.8%.

EXAMPLE 15

$Mo_{16}V_4Ta_2Fe_1$ or $Mo_1V_{0.25}Ta_{0.125}Fe_{0.0625}$

Seventy (70) grams of ammonium meta-vanadate (0.6 gram atoms of V) and 424 grams of ammonium paramolybdate (2.4 gram atoms of Mo) were dissolved in two liters of water while stirring at 60°–80° C., in a stainless steel beaker.

To the resulting solution were added 66 grams of tantalum oxalate solution (containing 0.3 gram atoms Ta) and 60 grams of ferric nitrate $Fe(NO_3)_3.9H_2O$ (0.15 gram atoms Fe) dissolved in 100 ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air.

The amount of catalyst deposited on the support calculated from the weight increase of the catalyst obtained is 19.2 wieght percent.

EXAMPLE 16

$Mo_{16}V_4Ta_2Mn_1$ or $Mo_1V_{0.25}Ta_{0.125}Mn_{0.0625}$

Two hundred eighty (280) grams of ammonium metavanadate (2.4 gram atoms of V) and 1696 grams of ammonium paramolybdate (9.6 gram atoms of Mo) were dissolved in 7.5 liters of water while stirring at 60°–80°, in a stainless steel evaporating dish.

To the resulting solution were added 1584 grams of tantalum oxalate sol (1.2 gram atoms Ta) and 216 grams of a 50.3% solution of manganous nitrate (0.6 gram atoms) dissolved in 200 ml water.

The resulting mixture was heated while stirring and 4160 grams (4000 ml) Norton silica-alumina SA 5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 19.2%.

Tantalum oxalate sol, containing the equivalent of 218.6 gm/l of $Ta_2O_5$ is a product of Kawecki Berylco Industries.

EXAMPLE 17

$Mo_{16}V_4Ti_2Mn_1$ or $Mo_1V_{0.25}Ti_{0.125}Mn_{0.0625}$

Seventy grams of ammonium meta-vandate (0.6 gram atoms of V) and 424 grams of ammonium paramolybdate (2.4 gram atoms of Mo) were dissolved in two liters of water while stirring at 60°–80° C., in a stainless steel beaker.

To the resulting solution was added 175 grams of titanium ammonium lactate (chelate) solution (containing 0.3 gram atoms Ti) and 54 grams of 50.3% manganese nitrate solution (0.15 gram atoms Mn) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.8 weight %.

EXAMPLE 18

$Mo_{16}V_4W_{1.6}Mn_4$ or $Mo_1V_{0.25}W_{0.1}Mn_{0.25}$

Three-hundred fifty (350) grams of ammonium meta-vanadate (3 gram atoms of V) and 2120 grams of ammonium paramolybdate (12 gram atoms of Mo) were dissolved in 10 liters of water while stirring at 60°–80°, in a stainless steel evaporating dish.

To the resulting solution were added 313 grams of ammonium paratungstate (1.13 gram atoms W) and 750 grams of manganous acetate tetrahydrate (3.06 gram atoms Mn) dissolved in 6000 ml water.

The resulting mixture was heated while stirring and was followed by drying by evaporation with stirring on a steam bath. Further drying was carried out at a temperature of 120° for a period of 24 hours.

The dried material was then transferred to a tray fabricated from 10-mesh stainless steel wire screen and calcined in a muffle furnace for 5 hours at 400° in an ambient atmosphere of air. The amount of unsupported catalyst thus obtained was 1453 grams. 2720 grams of dried material was obtained after the 120° C. drying step. 1636 grams of this dried material was calcined in the 400° C. calcination step to product 1453 grams of calcined catalyst.

EXAMPLE 19

$Mo_{16}Bi_{1.3}Ti_{1.3}Mn_{2.6}Si_{2.6}$ or $Mo_1Bi_{0.08}Ti_{0.08}Mn_{0.16}Si_{0.16}$

Four-hundred fifty-seven (457) grams of ammonium paramolybdate (2.6 gram atoms of Mo) were dissolved in 0.7 liters of water while stirring at 60°–80°, in a stainless steel evaporating dish.

To the resulting solution were added 249 grams of titanium lactate solution, "TYZOR LA" (0.21 g atoms Ti) and 104 grams of bismuth nitrate pentahydrate (0.21 gram atoms) dissolved in 110 ml water, containing 25 ml of concentrated nitric acid and 153 grams of a 50.3 percent solution of manganous nitrate (0.43 gram atoms of Mn), and then 86 grams of colloidal silica solution, LUDOX LS.

The resulting mixture was heated while stirring and 770 grams (1000 ml) Norton silica-alumina SA5205 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 32.5%.

TYZOR LA (T.M.) is a colloidal titanium lactate sol made by E. I. duPont de Nemours and Co. LUDOX LS (T.M.) is a colloidal silica solution made by E. I. duPont de Nemours and Co.

EXAMPLE 20

$Mo_{16}V_4Ta_{1.33}Fe_{0.67}Si_{1.33}$ or $Mo_1V_{0.25}Ta_{0.083}Fe_{0.042}Si_{0.083}$

Thirty-five point one (35.1) grams of ammonium meta-vanadate (0.3 gram atoms of V) and 212 grams of ammonium paramolybdate (1.2 gram atoms of Mo) were dissolved in 1.1 liters of water while stirring at 60°–80°, in a stainless steel evaporating dish.

To the resulting solution were added 126 grams of tantalum oxalate sol (containing the equivalent of 228 g $Ta_2O_5$/liter (0.1 gram atoms Ta) and 20.2 grams of ferric nitrate nonahydrate (0.05 gram atoms Fe) and 20 grams of LUDOX AS-30 (0.1 g atom Si) dissolved in 197 ml water.

The resulting mixture was heated while stirring and 770 grams (970 ml) Norton silica-alumina SA5205 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 22.5%.

EXAMPLE 21

$Mo_{16}V_4Ti_{1.3}Nb_{0.67}Mn_1$ or $Mo_1V_{0.25}Ti_{0.08}Nb_{0.042}Mn_{0.0625}$

Two hundred ten (210) grams of ammonium meta-vanadate (1.8 gram atoms of V) and 1272 grams of ammonium paramolybdate (7.2 gram atoms of Mo) were dissolved in 5.5 liters of water while stirring at 60°–80°, in a stainless steel evaporating dish.

To the resulting solution were added 351 grams of titanium ammonium lactate, "TYZOR LA" (0.6 gram atoms Ti) and 216 grams of niobium oxalate sol (0.3 gram atoms Nb) and 160 grams of a 50.3 percent solution of manganous nitrate (0.45 gram atoms Mn) dissolved in 200 ml water.

The resulting mixture was heated while stirring and 3120 grams (3000 ml) Norton silica-alumina SA5218 ¼" spheres were added. This was followed by drying by evaporating with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 37.8%.

EXAMPLE 22

$Mo_{16}Bi_{1.3}Fe_{1.3}Tl_{0.5}Ni_{7.3}Co_{1.3}Mg_{1.3}Mn_{2.1}P_{0.13}Si_{19.6}$ or $Mo_1Bi_{0.08}Fe_{0.08}Tl_{0.03}Ni_{0.456}Co_{0.08}Mg_{0.08}Mn_{0.131}P_{0.008}Si_{1.23}$

Zero point twenty-nine (0.29) grams of 85 percent phosphoric acid (0.0025 gram atoms of P) and 53 grams of ammonium paramolybdate (0.3 gram atoms of Mo) were dissolved in 0.3 liters of water while stirring at 60°–80°, in a porcelain evaporating dish. Sixty-seven (67) ml of a silica sol, LUDOX AS was then added and 50 ml conc. ammonium hydride.

To the resulting solution were added 10.1 grams of ferric nitrate nonahydrate 0.025 gram atoms Fe) 39.99 grams of nickel nitrate hexahydrate (0.1375 gram atoms Ni), 6.41 grams of magnesium nitrate hexahydrate (0.025 g atoms Mg), 7.25 grams of cobalt nitrate hexahydrate (0.025 g atoms Co), 14.27 grams of a 50.3 percent solution of manganous nitrate (0.025 g atoms Mn), 4.0 grams of thallium nitrate trihydrate (0.015 g atoms Tl) dissolved in 250 ml water.

The resulting mixture was heated while stirring and 12.13 grams of bismuth nitrate (0.025 g atoms Bi) dissoved in 30 ml water and 4 ml concentrated nitric acid were added. This was followed by drying by evaporation with stirring on a steam bath. Further drying was carried out at a temperature of 120° for a period of 16 hours.

The dried material was then transferred to a silica dish and calcined in a muffle furnace for 6 hours at 525° in an ambient atmosphere of air. The amount of unsupported catalyst obtained is 90 grams.

EXAMPLE 23

$Mo_{16}V_4Nb_2Cu_1$ or $Mo_1V_{0.25}Nb_{0.125}Cu_{0.0625}$

Forty-two (42) grams of ammonium meta-vanadate (0.36 gram atoms of V) and 254 grams of ammonium paramolybdate (1.44 gram atoms of Mo) were dissolved in 1.2 liters of water while stirring at 60°–80°, in a stainless steel evaporating dish.

To the resulting solution were added 158 grams of niobium oxalate (0.18 gram atoms Nb) and 22 grams of cupric nitrate (0.09 gram atoms Cu) dissolved in 60 ml water.

The resulting mixture was heated while stirring and 1040 grams (1000 ml) Norton silica-alumina SA5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 15.9%.

The catalyst of Example 23 was evaluated in Test Procedure B, and the test results are shown in Table I.

EXAMPLES 24–28

The catalysts of Examples 24–28 are outside the scope of the present invention. These catalysts were prepared as disclosed below, and tested in Catalyst Test Procedure A. When so tested they showed little or no selectivity for the purposes of converting ethane to ethylene. The catalysts of Examples 24–26 contained excess amounts of Fe and/or Co, i.e. $\geq 8$ gram atoms of Fe and/or Co per 16 gram atoms of Mo, and the catalysts of Examples 27–28 did not conain any Mo.

EXAMPLE 24

$Mo_{16}Co_{14}Mn_2$ or $Mo_1Co_{0.875}Mn_{0.125}$

One thousand five hundred fifty-six (1556) grams of ammonium paramolybdate (8.82 gram atoms of Mo) were dissolved in 4.16 liters of water while stirring at 60°–80°, in a stainless steel evaporating dish.

To the resulting solution were added 178.4 grams of manganese sulfate (1.06 gram atoms Mn) and 2328 grams of cobaltous nitrate (8 gram atoms Co) dissolved in 1760 ml water.

The resulting mixture was heated while stirring and 633 grams of titanium hydrate pulp was added. The slurry was neutralized with 677 grams of aqueous ammonium dissolved in 1243 ml of water. This was followed by drying by evaporation with stirring on a steam bath. Further drying was carried out at a temperature of 120° for a period of 16 hours.

The dried material was then transferred to an evaporating desk and calcined in a muffle furnace for 8 hours at 400° in an ambient atmosphere of air. The catalyst was pelletized and then roasted 12 hours at 550° C. Catalyst test results for this material by Procedure A showed no selectivity to ethylene, but complete combustion starting at 210° C.

EXAMPLE 25

$Mo_{16}Fe_{1.6}Co_{6.4}W_{3.2}Bi_{1.6}Si_{2.16}K_{0.1}$ or $Mo_1Fe_{0.1}Cr_{0.4}W_{0.2}Bi_{0.1}Si_{0.135}K_{0.06}$

Six hundred forty-eight (648) grams of ammonium paratungstate (2.483 gram atoms of W) and 2124 grams of ammonium paramolybdate (12.03 gram atoms of Mo) were dissolved in 3 liters of water while stirring at 60°–80°, in a stainless steel evaporating dish.

To the resulting solution were added 1400 grams of cobaltous nitrate hexahydrate (4.81 gram atoms of Co), 486 grams of ferric nitrate nonahydrate (1.203 gram atoms of Fe), and 584 grams of bismuth nitrate pentahydrate (1.204 g atoms of Bi), and 300 ml of a 1.35 percent potassium hydroxide solution (0.072 g atoms of K), dissolved in 1400 ml water.

The resulting mixture was heated while stirring and 320 grams of Ludox, a 30.5% colloidal silica sol were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The catalyst was mixed with 10 percent of its weight of naphthalene and pelleted into 5/16"×5/16" cylinders. The pellets were roasted 6 hours at 450° C. Catalyst test results for this material by Procedure A showed no selectivity to ethylene on oxidation of ethane at 366° C.

EXAMPLE 26

$Mo_{16}Fe_8$ or $Mo_1Fe_{0.5}$

Thirty-Five point three (35.3) grams of ammonium paramolybdate (0.2 gram atoms of Mo) were dissolved in 200 milliliters of water while stirring at 60°–80°, in a stainless steel evaporating dish. To the resulting solution were added 35 grams of ferric nitrate hexahydrate (0.1 gram atoms of Fe) dissolved in 200 ml water.

The resulting mixture was heated while stirring and then filtered. This was followed by drying at a temperature of 120° for a period of 16 hours.

The dried material was then transferred to a silica dish and calcined in a muffle furnace for 4 hours at 400° in an ambient atmosphere of pure oxygen. The amount of catalyst obtained is 34 grams. Catalyst test results for this material by Procedure A showed a reaction beginning at 276° C., but no selectivity for the production of ethylene.

EXAMPLE 27

$V_3Sb_{12}Ce_1$

Eight point seven (8.7) grams of vanadium pentoxide (0.096 gram atoms of V) was dissolved in 350 ml conc (16 N) hydrochloric acid and 200 ml ethanol while stirring at 55°, in a glass evaporating dish.

To the resulting solution were added 114.4 grams of antimony pentachloride (0.383 gram atoms Sb) dissolved in 80 ml conc HCl and 13.847 grams of cerium nitrate hexahydrate (0.032 gram atoms of Ce) dissolved in 100 ml ethanol.

The resulting mixture was neutralized with 440 ml conc ammonium hydroxide dissolved in 700 ml of water. The precipitate was filtered and washed on the filter with 1000 ml water. This was followed by drying at a temperature of 120° for a period of 16 hours.

The dried material was then transferred to a tray fabricated from 10-mesh stainless steel wire screen and calcined in a muffle furnace for 12 hours at 750° in an ambient atmosphere of air. Catalyst test results for this material by Procedure A showed activity to burn ethane at 262° C., but no selectivity for the formation of ethylene.

EXAMPLE 28

$Sb_5V_1Nb_1Bi_5$

Twenty-eight (28) grams of ammonium metavanadate (0.2404 gram atoms of V) were dissolved in 700 ml of water while stirring at 60°–80°, in a stainless steel evaporating dish.

To the resulting solution were added 583 grams of bismuth nitrate pentahydrate (1.202 gram atoms Bi) and 180 grams of antimony trioxide (1.202 gram atoms Sb) and 219 grams (172 ml) of niobium oxalate sol (0.2404 g atoms Nb) dissolved in 720 ml of 3 N nitric acid.

The resulting mixture was heated while stirring and 770 grams (1000 ml) Norton silica-alumina SA5205 ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 36.1%.

When tested in Catalyst Test Procedure A, the catalyst of Example 28 showed initial activity at 525° C. However, the % selectivity of ethane to ethylene at this temperature was only 26%.

TABLE 1

Results of Catalyst Tests - Procedure A (or B*)

| Example No. | Catalyst Composition | Temp. of Initial Activity °C. (To) | Selectivity to $C_2H_4$, % at To | Temp. for 10% Conversion of $C_2H_6$, °C. ($T_{10}$) | Selectivity to $C_2H_4$, %, at $T_{10}$ |
|---|---|---|---|---|---|
| 1 | Mo | 418 | 100 | 500 | 88 |
| 2 | $Mo_{16}Mn_{16}$ | 320 | 100 | 550–600 | 35 |
| 3 | $Mo_{16}Nb_4$ | 516 | 100 | 634 | 74 |
| 4 | $Mo_{16}Ti_4$ | 390 | 100 | 600 | 65 |
| 5 | $Mo_{16}V_{1.4}$ | 444 | Ca.100 | 562 | 59 |
| 6 | $Mo_{16}V_4$ | 500 | 100 | 540 | 100 |
| 7 | $Mo_{16}W_{5.3}$ | 388 | 100 | 650 | 78 |
| 8 | $Mo_{16}V_4Fe_1$ | 370 | 100 | 435 | 87 |
| 9 | $Mo_{16}V_4Mn_4$ | 502 | 100 | 505 | 100 |
| 10 | $Mo_{16}V_4Nb_2$ | 215 | 100 | 286 | 100 |
| 11 | $Mo_{16}W_2Nb_4$ | Ca 400 | — | 524 | 67 |
| 12 | $Mo_{16}W_{3.3}Pb_{1.9}$ | 474 | >80 | 588 | 72 |
| 13 | $Mo_{16}Nb_4W_{1.6}Mn_4$ | 328 | ca 100 | 400 | 10 |
| 14 | $Mo_{16}V_4Nb_1Mn_1$ | 243 | 100 | 300 | 100 |
| 15 | $Mo_{16}V_4Ta_2Fe_1$ | 310 | 100 | 418 | 97 |
| 16* | $Mo_{16}V_4Ta_2Mn_1$ | 309 | 85 | 385 | 63 |
| 17 | $Mo_{16}V_4Ti_2Mn_1$ | 215 | 100 | 295 | 100 |
| 18 | $Mo_{16}V_4W_{1.6}Mn_4$ | <255 | 100 | 295 | 100 |
| 19 | $Mo_{16}Bi_{1.3}Ti_{1.3}Mn_{2.6}Si_{2.6}$ | 460 | 100 | 505 | 100 |
| 20 | $Mo_{16}V_4Ta_{1.33}Fe_{0.67}Si_{1.33}$ | 220 | 100 | 289 | 88 |
| 21* | $Mo_{16}V_4Ti_{1.3}Nb_{0.67}Mn_1$ | 260 | 84 | 400 | 80 |
| 22 | $Mo_{16}Bi_{1.3}Fe_{1.3}Tl_{0.5}Ni_{7.3}Co_{1.3}$ $Mg_{1.3}Mn_{2.1}P_{0.13}Si_{19.6}$ | 422 | 100 | >600 | <21 |
| 23* | $Mo_{16}V_4Nb_2Cu_1$ | 260 | 95 | 330 | 78 |

EXAMPLES 29-46

Catalysts 29-46 were prepared as disclosed below, and evaluated in Catalyst Test Procedure B. Each of the catalysts of Examples 29-31 contain the elements Mo and V, and the catalysts of Examples 32-46 contain the elements Mo and V and one other X or Y element. The composition of each catalyst is given at the headings of the respective Examples, and the test results are given in Table II below.

Each catalyst of Examples 29-46 was evaluated at one or two different hot spot temperatures between 300 and 400° C. to determine the % conversion and % efficiency results at each such temperature for oxydehydrogenating ethane to ethylene.

EXAMPLE 29

$Mo_{16}V_4$ or $Mo_1V_{0.25}$ 40.9 Grams of ammonium meta-vanadate (0.35 gram atoms of V) was dissolved in 1 liter of water while stirring at 85°-95°, in a stainless steel steam jacketed evaporating dish.

To the resulting solution were added 40.9 grams of oxalic acid (0.454 mols) in 400 ml water and 247 grams of ammonium paramolybdate (1.4 gram atoms Mo) dissolved in 800 ml water.

The resulting mixture was heated while stirring and dried by evaporation with stirring. Further drying was carried out at a temperature of 120° for a period of 16 hours.

The dried material was broken to 4×8 mesh then transferred to a tray fabricated from 10-mesh stainless steel wire screen and calcined in a muffle furnace for 4 hours at 400° in an ambient atmosphere of air. This was a neat catalyst; no support was added.

EXAMPLE 30

$Mo_{16}V_{6.7}$ or $Mo_1V_{0.42}$

57 Grams of ammonium meta-vanadate (0.487 gram atoms of V) was dissolved in 1.5 liters of water (90°); added 66 grams of glycerol and 216 grams of ammonium paramolybdate dissolved in 220 ml water (1.22 gram atoms of Mo) while stirring at 60°-80°, in a stainless steel evaporating dish.

The resulting mixture was heated while stirring and 1000 grams (1000 ml) Norton silica-alumina #5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere or air. The amount of catalyst deposited on the support calculated from the weight increase of the catalyst obtained is 18.5%.

EXAMPLE 31

$Mo_{16}V_8$ or $Mo_1V_{0.5}$

16 Grams of ammonium meta-vanadate (0.136 gram atoms V) and 48.1 grams of ammonium paramolybdate (0.272 gram atoms Mo) were dissolved in 0.5 liters of water while stirring at 85°-95°, in a stainless steel steam jacketed evaporating dish.

To the resulting solution were added 4.8 grams of ammonium oxalate, [$(NH_4)_2C_2O_4.H_2O$] (0.034 mols) in 50 ml water.

The resulting mixture was heated while stirring and 140 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 22%.

EXAMPLE 32

$Mo_{16}V_8Fe_1$ or $Mo_1V_{0.5}Fe_{0.0625}$ 15.9 Grams of ammonium meta-vanadate (0.136 gram atoms of V) and 48.1 grams of ammonium paramolybdate (0.272 gram atoms of Mo) were dissolved in 0.3 liters of water while stirring at 85°-95°, in a stainless steel steam jacketed evaporating dish.

To the resulting solution were added 4.8 grams of ferric sulfate ($Fe_2[SO_4]_3.9H_2O$) (0.017 gram atoms of Fe) in 400 ml water.

The resulting mixture was heated while stirring and 130 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 27.4%. Catalyst test results for this material are given in Table II.

EXAMPLE 33

$Mo_{16}V_2Nb_2$ or $Mo_1V_{0.125}Nb_{0.125}$

16 Grams of ammonium meta-vanadate (0.136 gram atoms of V) and 192.4 grams of ammonium paramolybdate (1.09 gram atoms of Mo) were dissolved in 0.8 liters of water while stirring at 85°-95°, in a stainless steel steam jacketed evaporating dish.

To the resulting solution were added 124 grams of niobium oxalate solution (14.6% $Nb_2O_5$) in 100 ml water (0.136 gram atoms of Nb).

The resulting mixture was heated while stirring and dried by evaporation with stirring. Further drying was carried out at room temperature under total vacuum for a period of 3 days.

The dried material was broken to 4×8 mesh and then transferred to a tray fabricated from 10-mesh stainless steel wire screen and calcined in a muffle furnace for 4 hours at 400° in an ambient atmosphere of air. This was a neat catalyst; no support was added.

EXAMPLE 34

$Mo_{16}V_4Nb_2$ or $Mo_1V_{0.25}Nb_{0.125}$ 40.9 Grams of ammonium meta-vanadate (0.350 gram atoms of V) was dissolved in 1.0 liters of water while stirring at 85°-95° C., in a stainless steel steam jacketed evaporating dish.

To the resulting solution were added 159.2 grams of niobium oxalate solution (14.6% $Nb_2O_5$) diluted with 100 ml water (0.175 gram atoms of Nb) and 247 grams of ammonium paramolybdate (1.399 gram atoms of Mo) dissolved in 800 ml water.

The resulting mixture was heated and dried by evaporation with stirring. Further drying was carried out at a temperature of 120° for a period of 16 hours.

The dried material was broken to 4×8 mesh and then transferred to a tray fabricated from 10-mesh stainless steel wire screen and calcined in a muffle furnace for 4 hours at 400° in an ambient atmosphere of air. This was a neat catalyst; no support was added.

EXAMPLE 35

$Mo_{16}V_{4.6}Nb_{0.6}$ or $Mo_1V_{0.288}Nb_{0.0375}$ 81.8 Grams of ammonium meta-vanadate (0.7 gram atoms of V) and 494 grams of ammonium paramolybdate (2.8 gram atoms of Mo) were dissolved in 1.5 liters of water while stirring at 85°–95°, in a stainless steel steam jacketed evaporating dish.

To the resulting solution were added 318.4 grams of niobium oxalate solution (14.6% $Nb_2O_5$) in 200 ml water (0.35 gram atoms Nb). The resultant slurry was filtered; the filtrate allowed to stand at room temperature for 3 days. More crystals formed and were filtered out. The final filtrate was evaporated to dryness, with stirring, in the stainless steel evaporator. Further drying was carried out at a temperature of 120° for a period of 16 hours.

The dried material was broken to 4×8 mesh and then transferred to a tray fabricated from 10-mesh stainless steel wire screen and calcined in a muffle furnace for 4 hours at 400° in an ambient atmosphere of air. This was a neat catalyst; no support was added. Analysis indicates the composition $Mo_{16}V_{4.6}Nb_{0.6}$.

EXAMPLE 36

$Mo_{16}V_6Nb_2$ or $Mo_1V_{0.375}Nb_{0.125}$ 61.4 Grams of ammonium meta-vanadate (0.525 gram atoms of V) was dissolved in 1.0 liters of water while stirring at 85°–95° C., in a stainless steel steam jacketed evaporating dish.

To the resulting solution were added 275 grams of niobium oxalate solution (8.45% $Nb_2O_5$) (0.175 gram atoms Nb) and 247 grams of ammonium paramolybdate (1.399 gram atoms Mo) dissolved in 800 ml water.

The resulting mixture was heated and dried by evaporation with stirring. Further drying was carried out at a temperature of 120° for a period of 16 hours.

The dried material was broken to 4×8 mesh and then transferred to a tray fabricated from 10-mesh stainless steel wire screen and calcined in a muffle furnace for 4 hours at 400° in an ambient atmosphere of air. This was a neat catalyst; no support was added.

EXAMPLE 37

$Mo_{16}V_8Nb_{0.5}$ or $Mo_1V_{0.5}Nb_{0.031}$

16 Grams of ammonium meta-vanadate (0.136 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution was added 7.75 grams of niobium oxalate solution (14.6% $Nb_2O_5$) (0.0085 gram atoms Nb).

The resulting mixture was heated while stirring and 140 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 23.2%.

EXAMPLE 38

$Mo_{16}V_8Nb_2$ or $Mo_1V_{0.5}Nb_{0.125}$ 15.9 Grams of ammonium meta-vanadate (0.136 gram atoms of V) and 48.1 grams of ammonium paramolybdate (0.272 gram atoms of Mo) were dissolved in 0.5 liters of water while stirring at 85°–95° C., in a stainless steel steam jacketed evaporating dish.

To the resulting solution was added 31.0 grams of niobium oxalate solution (14.6% $Nb_2O_5$) (0.034 gram atoms Nb).

The resulting mixture was heated while stirring and 145 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 19.7%.

EXAMPLE 39

$Mo_{16}V_{12.9}Nb_{10.1}$ or $Mo_1V_{0.806}Nb_{0.63}$ 22.5 grams of ammonium meta-vanadate (0.192 gram atoms of V) and 42.1 grams of ammonium paramolybdate (0.238 gram atoms of Mo) were dissolved in 0.5 liters of water while stirring at 85°–95°, in a stainless steel steam jacketed evaporating dish.

To the resulting solution were added 137.7 grams of niobium oxalate solution (14.6% $Nb_2O_5$) (0.151 gram atoms Nb) and 12.6 grams of ammonium nitrate ($NH_4NO_3$) (0.157 mols).

The resulting mixture was heated while stirring and 160 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 20.3%.

EXAMPLE 40

$Mo_{16}V_{21.3}Nb_{3.7}$ or $Mo_1V_{1.33}Nb_{0.23}$ 42.4 Grams of ammonium meta-vanadate (0.362 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 57.4 grams of niobium oxalate solution (14.6% $Nb_2O_5$) (0.063 gram atoms Nb) and 5.0 grams of ammonium nitrate ($NH_4NO_3$) (0.062 mols) dissolved in 30 ml water.

The resulting mixture was heated while stirring and 160 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 24.2%.

EXAMPLE 41

$Mo_{16}V_4Sb_2$ or $Mo_1V_{0.25}Sb_{0.125}$

70 Grams of ammonium meta-vanadate (0.6 gram atoms of V) and 424 grams of ammonium paramolybdate (2.4 grams atoms of Mo) were dissolved in 2.0 liters of water while stirring at 60°–80°, in a stainless steel evaporating dish.

To the resulting solution were added 95 grams of oxalic acid (in 500 ml water) (0.75 mols $H_2C_2O_4$) and 370 grams of colloidal antimony oxide (10% Sb) (0.3 gram atoms Sb).

The resulting mixture was heated while stirring and 1040 grams (1000 ml) Norton silica-alumina #5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 16.8%.

EXAMPLE 42

$Mo_{16}V_4Si_{32}$ or $Mo_1V_{0.25}Si_2$ 23.9 Grams of ammonium meta-vanadate (0.204 gram atoms of V) and 144.3 grams of ammonium paramolybdate (0.817 gram atoms of Mo) were dissolved in 0.5 liters of water while stirring at 85°–95°, in a stainless steel steam jacketed evaporating dish.

To the resulting solution were added 326 grams of "Ludox AS" (30.1% $SiO_2$) (1.633 gram atoms Si).

The resulting mixture was heated while stirring and dried by evaporation with stirring. Further drying was carried out at a temperature of 120° for a period of 16 hours.

The dried material was broken to 4×8 mesh and then transferred to a tray fabricated from 10-mesh stainless steel wire screen and calcined in a muffle furnace for 4 hours at 400° in an ambient atmosphere of air. This was a neat catalyst; no support was added.

EXAMPLE 43

$Mo_{16}V_8Sn_2$ or $Mo_1V_{0.5}Sn_{0.125}$ 16.0 Grams of ammonium meta-vanadate (0.137 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 7.7 grams of stannous chloride ($SnCl_2.2H_2O$) (0.034 gram atoms Sn) in 120 ml water and 5 ml concentrated hydrochloric acid.

The resulting mixture was heated while stirring and 140 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 23.1%.

EXAMPLE 44

$Mo_{16}V_8Ta_2$ or $Mo_1V_{0.5}Ta_{0.125}$ 16.0 Grams of ammonium meta-vanadate (0.137 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution was added 43.3 grams of tantalum oxalate solution (17.38% $Ta_2O_5$) diluted with 100 ml water (0.034 gram atoms Ta).

The resulting mixture was heated while stirring and 140 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 23.4%.

EXAMPLE 45

$Mo_{16}V_4Ti_2$ or $Mo_1V_{0.25}Ti_{0.125}$

82 Grams of ammonium meta-vanadate (0.7 gram atoms of V) and 494 grams of ammonium paramolybdate (2.8 gram atoms of Mo) were dissolved in 2.0 liters of water while stirring at 60°–80°, in a stainless steel evaporating dish.

To the resulting solution were added 204 grams of "TYZOR" LA (titanium lactate) 8.2% Ti (0.35 gram atoms Ti) and 28 grams of ammonium nitrate (0.35 moles $NH_4NO_3$) dissolved in 100 ml water.

The resulting mixture was heated while stirring and 1040 grams (1000 ml) Norton silica-alumina #5218 ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 30.4%.

EXAMPLE 46

$Mo_{16}V_8W_2$ or $Mo_1V_{0.5}W_{0.125}$ 15.9 Grams of ammonium meta-vanadate (0.136 gram atoms of V) and 48.1 grams of ammonium paramolybdate (0.272 gram atoms of Mo) were dissolved in 500 millimeters of water while stirring at 85°–95°, in a stainless steel steam jacketed evaporating dish.

To the resulting solution were added 8.6 grams of ammonium metatungstate 92% $WO_3$ (in 100 ml water) (0.034 gram atom W).

The resulting mixture was heated while stirring and 145 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 26.1%.

TABLE II

Results of Tests on Catalysts 29–46 by Catalyst Test Procedure B

| Ex. | Catalyst Composition | Metal Oxides in Catalyst, % | Catalyst Hot Spot, °C. | Ethane Conversion % | Efficiency to Ethylene, % |
|---|---|---|---|---|---|
| 29 | $Mo_{16}V_4$ | 100 | 300 | 2 | 87 |
| 30 | $Mo_{16}V_{6.7}$ | 18.5 | 325 | 4 | 78 |
|    |              |      | 400 | 22 | 47 |
| 31 | $Mo_{16}V_8$ | 22 | 305 | trace | — |
|    |              |    | 400 | 9 | 45 |
| 32 | $Mo_{16}V_8Fe_1$ | 27.4 | 300 | trace | — |
|    |              |      | 400 | 9 | 45 |
| 33 | $Mo_{16}V_2Nb_2$ | 100 | 300 | 12 | 86 |
| 34 | $Mo_{16}V_4Nb_2$ | 100 | 300 | 29 | 83 |
| 35 | $Mo_{16}V_{4.6}Nb_{0.6}$ | 100 | 300 | 29 | 81 |
|    |              |      | 378 | 65 | 51 |
| 36 | $Mo_{16}V_6Nb_2$ | 100 | 300 | 28 | 83 |
| 37 | $Mo_{16}V_8Nb_{0.5}$ | 23.2 | 322 | 1.4 | 100 |
|    |              |      | 400 | 12 | 76 |
| 38 | $Mo_{16}V_8Nb_2$ | 19.7 | 300 | 12 | 91 |
|    |              |      | 400 | 50 | 68 |
| 39 | $Mo_{16}V_{12.9}Nb_{10.1}$ | 20.3 | 300 | trace | — |
|    |              |      | 400 | 8 | 85 |
| 40 | $Mo_{16}V_{21.3}Nb_{3.7}$ | 24.2 | 315 | 2 | 83 |
|    |              |      | 400 | 20 | 46 |
| 41 | $Mo_{16}V_4Sb_2$ | 16.8 | 300 | 6 | 95 |
|    |              |      | 400 | 23 | 75 |
| 42 | $Mo_{16}V_4Si_{32}$ | 100 | 300 | 1 | 99 |
|    |              |      | 400 | 14 | 50 |
| 43 | $Mo_{16}V_8Sn_2$ | 23.1 | 328 | trace | — |
|    |              |      | 400 | 7 | 52 |
| 44 | $Mo_{16}V_8Ta_2$ | 23.4 | 300 | 4 | 85 |
|    |              |      | 400 | 25 | 69 |
| 45 | $Mo_{16}V_4Ti_2$ | 30.4 | 300 | 2 | 77 |
|    |              |      | 400 | 15 | 55 |
| 46 | $Mo_{16}V_8W_2$ | 26.1 | 300 | trace | — |
|    |              |      | 400 | 7 | 61 |

EXAMPLES 47–58

Catalysts 47–58 were prepared as disclosed below, and evaluated in Catalyst Test Procedure B. Each of the catalysts of Examples 47–57 contain the elements Mo, V and Nb and one other X or Y element. The catalyst of Example 58 contains the elements Mo and V, and W and Mn. The composition of each catalyst is given at the heading of the respective Examples, and the test results are given in Table III below.

Each catalyst of Examples 47–58 was evaluated at two hot spot temperatures between 300° and 400° C. to determine the % conversion and % efficiency results at each such temperature for oxydehydrogenating ethane to ethylene.

EXAMPLE 47

$Mo_{16}V_4Nb_2K_{0.5}$ or $Mo_1V_{0.25}Nb_{0.125}K_{0.031}$ 8.0 Grams of ammonium meta-vanadate (0.068 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 0.85 grams of potassium nitrate ($KNO_3$) (0.0084 gram atoms K) and 31 grams of niobium oxalate solution (14.6% $Nb_2O_5$) 0.034 gram atoms Nb) and 2.8 grams ammonium nitrate ($NH_4NO_3$) (0.035 mols).

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 17.9%.

EXAMPLE 48

$Mo_{16}V_4Nb_4P_4$ or $Mo_1V_{0.25}Nb_{0.25}P_{0.25}$

8 Grams of ammonium meta-vanadate (0.068 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 7.8 grams of phosphoric acid (85.6% $H_3PO_4$) (0.068 gram atoms P) and 62 grams of niobium oxalate solution (14.6% $Nb_2O_5$) (0.068 gram atoms Nb) and 5.6 grams ammonium nitrate (0.07 mols $NH_4NO_3$).

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 25.3%.

EXAMPLE 49

$Mo_{16}V_8Nb_2Ce_2$ or $Mo_1V_{0.5}Nb_{0.125}Ce_{0.125}$ 15.9 Grams of ammonium meta-vanadate (0.136 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 31 grams of niobium oxalate solution (14.6% $Nb_2O_5$) in 100 ml water (0.034 gram atoms Nb) and 14 grams of cerium nitrate (41.8% CeO$_2$) (0.034 gram atoms Ce) dissolved in 150 ml water.

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 28%.

EXAMPLE 50

$Mo_{16}V_8Nb_2Co_2$ or $Mo_1V_{0.5}Nb_{0.125}Co_{0.125}$ 15.9 Grams of ammonium meta-vanadate (0.136 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 31 grams of niobium oxalate solution (14.6% Nb$_2$O$_5$) in 100 ml water (0.034 gram atoms Nb) and 8.5 grams of cobalt acetate, [Co(CH$_3$COO)$_2$.4H$_2$O] (0.034 gram atoms Co) dissolved in 150 ml water.

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 26.3%.

EXAMPLE 51

$Mo_{16}V_8Nb_2Cr_2$ or $Mo_1V_{0.5}Nb_{0.125}Cr_{0.125}$ 15.9 Grams of ammonium meta-vanadate (0.136 gram atoms of V) and 48.1 grams of ammonium paramolybdate (0.272 gram atoms of Mo) were dissolved in 0.6 liters of water while stirring at 85°–95°, in a stainless steel steam jacketed evaporating dish.

To the resulting solution were added 31 grams of niobium oxalate solution (14.6% Nb$_2$O$_5$) in 100 ml water (0.034 gram atoms Nb) and 8.4 grams of chromium acetate, [Cr(C$_2$H$_3$O$_2$)$_3$.H$_2$O] (0.034 gram atoms Cr) dissolved in 150 ml water.

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 24.2%.

EXAMPLE 52

$Mo_{16}V_8Nb_2Cu_2$ or $Mo_1V_{0.5}Nb_{0.125}Cu_{0.125}$ 15.9 Grams of ammonium meta-vanadate (0.136 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 31 grams of niobium oxalate solution (14.6% Nb$_2$O$_5$) in 100 ml water (0.034 gram atoms Nb) and 6.8 grams of cupric acetate, [(CH$_3$COO)$_2$Cu.H$_2$O] (0.034 gram atoms Cu) dissolved in 150 ml water.

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 25.1%.

EXAMPLE 53

$Mo_{16}V_8Nb_2Fe_2$ or $Mo_1V_{0.5}Nb_{0.125}Fe_{0.125}$ 15.9 Grams of ammonium meta-vanadate (0.136 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 31 grams of niobium oxalate solution (14.6% Nb$_2$O$_5$) in 100 ml water (0.034 gram atoms Nb) and 6.4 grams of ferric oxalate, [Fe$_2$(C$_2$O$_4$)$_3$] (0.034 gram atoms Fe) dissolved in 150 ml water plus 4.4 grams of oxalic acid.

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 23%.

EXAMPLE 54

$Mo_{16}V_8Nb_2Mn_2$ or $Mo_1V_{0.5}Nb_{0.125}Mn_{0.125}$ 15.9 Grams of ammonium meta-vanadate (0.136 gram atoms of V) and 48.1 grams of ammonium paramolybdate (0.272 gram atoms of Mo) were dissolved in 0.4 liters of water while stirring at 85°–95°, in a stainless steel steam jacketed evaporating dish.

To the resulting solution were added 31 grams of niobium oxalate solution (14.6% Nb$_2$O$_5$) (0.034 gram atoms Nb) and 8.4 grams of manganese acetate, (0.034 gram atoms Mn) dissolved in 100 ml water.

The resulting mixture was heated while stirring and 140 grams (Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 25.4%.

EXAMPLE 55

$Mo_{16}V_8Nb_2Ni_2$ or $Mo_1V_{0.5}Nb_{0.125}Ni_{0.125}$ 15.9 Grams of ammonium meta-vanadate (0.136 gram atoms of V) and 48.1 grams of ammonium paramolybdate (0.272 gram atoms of Mo) were dissolved in 0.5 liters of water while stirring at 85°–95°, in a stainless steel steam jacketed evaporating dish.

To the resulting solution were added 31 grams of niobium oxalate solution (14.6% $Nb_2O_5$) in 100 ml water (0.034 gram atoms Nb) and 8.5 grams of nickelous acetate ($Ni(C_2H_3O_2)_2.4H_2O$), (0.034 gram atoms Ni) dissolved in 150 ml water.

The resulting mixture was heated while stirring and 150 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated for 10-mesh stainless steel wire screen and calcined in a muffle furnace for 4 hours at 400° in an ambient atmosphere of air. The amount of catalyst deposited on the support calculated from the weight increase of the catalyst obtained is 26.4%.

EXAMPLE 56

$Mo_{16}V_8Nb_2Si_{32}$ or $Mo_1V_{0.5}Nb_{0.125}Si_2$ 35.9 Grams of ammonium meta-vanadate (0.307 grams atoms of V) and 108.0 grams of ammonium paramolybdate (0.612 gram atoms of Mo) were dissolved in 0.5 liters of water while stirring at 85°–95°, in a stainless steel steam jacketed evaporating dish.

To the resulting solution were added 69.6 grams of niobium oxalate solution (14.6% $Nb_2O_5$), (0.076 gram atoms Nb) and 244.2 grams of "Ludox AS" colloidal silica sol (30.1% $SiO_2$), (1,223 gram atoms Si).

The resulting mixture was heated while stirring and dried by evaporation with stirring. Further drying was carried out at a temperature of 120° for a period of 16 hours.

The dried material was broken to 4×8 mesh and was then transferred to a tray fabricated from 10-mesh stainless steel wire screen and calcined in a muffle furnace for 4 hours at 400° in an ambient atmosphere of air. This was a neat catalyst; no support was added.

EXAMPLE 57

$Mo_{16}V_8Nb_2U_1$ or $Mo_1V_{0.5}Nb_{0.125}U_{0.0625}$ 15.9 Grams of ammonium meta-vanadate (0.136 gram atoms of V) and 48.1 grams of ammonium paramolybdate (0.272 gram atoms of Mo) were dissolved in 0.35 liters of water while stirring at 85°–95° C., in a stainless steel steam jacketed evaporating dish.

To the resulting solution were added 31 grams of niobium oxalate solution (14.6% $Nb_2O_5$) (0.034 gram atoms Nb) and 7.2 grams of uranyl acetate, $[(CH_3COO)_2UO_2.2H_2O]$ (0.017 gram atoms U).

The resulting mixture was heated while stirring and 140 grams Norton silica-alumina #5218 4×8 mesh (irregular shapes) were added. This was followed by drying by evaporation with stirring. Further drying was carried out at a temperature of 120° for a period of 16 hours.

The dried material was then transferred to a tray fabricated from 10-mesh stainless steel wire screen and calcined in a muffle furnace for 4 hours at 400° in an ambient atmosphere of air. The amount of catalyst deposited on the support calculated from the weight increase of the catalyst obtained is 27%.

EXAMPLE 58

$Mo_{16}V_4W_{1.6}Mn_4$ or $Mo_1V_{0.25}W_{0.1}Mn_{0.25}$ 350 grams of ammonium meta-vanadate (3 gram atoms of V) and 2120 grams of ammonium paramolybdate (12.0 gram atoms of Mo) were dissolved in 10 liters of water while stirring at 60°–80°, in a stainless steel evaporating dish.

To the resulting solution were added 313 grams of ammonium paratungstate dissolved in 5 liters water (1.13 gram atoms W) and 750 grams of manganese acetate .$4H_2O$ (3.06 gram atoms Mn) dissolved in 1 liter water.

The resulting mixture was heated while stirring and dried by evaporation with stirring. Further drying was carried out at a temperature of 120° for a period of 16 hours.

The dried material was broken to 4×8 mesh and then transferred to a tray fabricated from 10-mesh stainless steel wire screen and calcined in a muffle furnace for 5 hours at 400° in an ambient atmosphere of air. This was a neat catalyst.

TABLE III

Results of Tests on Catalysts 47–58 by Catalyst Test Procedure B

| Ex. | Catalyst Composition | Metal Oxides in Catalyst, % | Catalyst Hot Spot, °C. | Ethane Conversion % | Efficiency to Ethylene, % |
|---|---|---|---|---|---|
| 47 | $Mo_{16}V_4Nb_2K_{0.5}$ | 17.9 | 338 | 6 | 89 |
|   |   |   | 400 | 24 | 73 |
| 48 | $Mo_{16}V_4Nb_4P_4$ | 25.3 | 319 | trace | — |
|   |   |   | 378 | 3.3 | 58 |
| 49 | $Mo_{16}V_8Nb_2Ce_2$ | 28 | 300 | 8.6 | 84 |
|   |   |   | 400 | 39.4 | 56 |
| 50 | $Mo_{16}V_8Nb_2Co_2$ | 26.3 | 300 | 6 | 94 |
|   |   |   | 400 | 29 | 59 |
| 51 | $Mo_{16}V_8Nb_2Cr_2$ | 24.2 | 300 | 2.2 | 87 |
|   |   |   | 400 | 13.5 | 65 |
| 52 | $Mo_{16}V_8Nb_2Cu_2$ | 25.1 | 300 | 6 | 79 |
|   |   |   | 400 | 42 | 52 |
| 53 | $Mo_{16}V_8Nb_2Fe_2$ | 23 | 300 | 8 | 82 |
|   |   |   | 400 | 42 | 57 |
| 54 | $Mo_{16}V_8Nb_2Mn_2$ | 25.4 | 300 | 4 | 97 |
|   |   |   | 400 | 28 | 74 |
| 55 | $Mo_{16}V_8Nb_2Ni_2$ | 26.4 | 300 | 5 | 93 |
|   |   |   | 400 | 33 | 59 |
| 56 | $Mo_{16}V_8Nb_2Si_{32}$ | 100 | 300 | 13 | 82 |
|   |   |   | 400 | 50 | 50 |
| 57 | $Mo_{16}V_8Nb_2U_1$ | 27 | 300 | 12 | 91 |
|   |   |   | 400 | 53 | 64 |
| 58 | $Mo_{16}V_4W_{1.6}Mn_4$ | 100 | 300 | 8 | 58 |
|   |   |   | 400 | 58 | 58 |

EXAMPLES 59–61

The catalyst of Example 35 ($Mo_{16}V_{4.6}Nb_{0.6}$) was used in three experiments (Examples 59–61) in the oxydehydrogenation of ethane to ethylene, in the absence or presence of added water, to demonstrate the ability of such catalyst to prepare acetic acid under such conditions. No water was added in Examples 59–60. Water was added in Example 61. The reaction conditions employed (pressure, temperature, inlet gas composition, inlet water rate and outlet water rate), and the test results (% selectivity, productivity and % conversion) for these examples are shown below in Table IV. The catalyst was evaluated in Examples 59–61 by Catalyst Test Procedure C.

TABLE IV

Oxydehydrogenation of Ethane With The Catalyst $Mo_{16}V_{4.6}Nb_{0.6}$ Showing Production of Acetic Acid

| Example | Total Pressure psig | Reaction Temperature °C. | Inlet gas Composition* $O_2$, % | Inlet gas Composition* $C_2H_6$, % | Inlet $H_2O$ Rate (moles hr$^{-1}$) | Outlet $H_2O$ Rate (moles hr$^{-1}$) | Ethane Conversion, % | Eff. to $C_2H_4$, % | $C_2H_4$ Productivity, lbs/ft$^3$ cat/hr | Eff. to $CH_3COOH$ % | $CH_3COOH$ Productivity, lbs/ft$^3$ cat hr |
|---|---|---|---|---|---|---|---|---|---|---|---|
| 59 | 75 | 275 | 3.2 | 89.1 | 0.0 | 0.37 | 3.1 | 85.0 | 3.8 | 13.2 | 1.3 |
| 60 | 75 | 322 | 6.0 | 90.0 | 0.0 | 0.83 | 6.9 | 73.1 | 7.2 | 18.8 | 4.0 |
| 61 | 125 | 323 | 6.5 | 85.8 | 0.98 | 1.5 | 7.5 | 67.6 | 8.2 | 18.4 | 4.8 |

It is believed that two groups of catalysts which are exemplified in various of the examples disclosed above are novel compositions of matter, supported and unsupported. These catalysts comprise the following compositions:

Novel Catalyst I $$Mo_hV_iNb_jA_k$$

wherein
A is Ce, K, P, Ni, and/or U,
h is 16,
i is 1 to 16, and preferably 1 to 8,
j is 1 to 10, and preferably 0.2 to 10,
k is >0 to 32, and preferably 0.1 to 5.

Novel Catalyst II $$Mo_lW_mL_n$$

wherein
L is Nb and/or Pb,
l is 16,
m is 1 to 16, and preferably 1 to 8,
n is 1 to 10, and preferably 0.2 to 10.

In the catalyst evaluation tests conducted in Examples 1–23 and 29–61 the effluent gas streams did not contain any hydrogen, methane or higher alkanes produced by the process. The products formed in all cases were ethylene, acetic acid, water, CO and $CO_2$.

What is claimed is:

1. A low temperature process for converting ethane to ethylene which comprises catalytically oxydehydrogenating ethane exothermically at a temperature of 450° C. or less in the gas phase in which the catalyst is a calcined composition containing the elements of Mo, X, and Y in the ratio:

$$Mo_aX_bY_c$$

wherein X is at least one of the groups V, Nb and Mn; V and W; V and Mn; or W and Nb.
Y is selected from the group consisting of Bi, Ce, Co, Cu, Fe, K, Mg, Ni, P, Pb, Sb, Si, Sn, Tl and/or U,
a is 1
b is 0.05 to 1
c is 0 to 2
with the proviso that the total value of c for Fe, Co and/or Ni is less than 0.5.

2. A process as in claim 1 in which X in said calcined composition also comprises the elements Ta and/or Ti; Y comprises the elements Fe, Sb, Si, and Sn, and b and c are 0.05 to 1; with the proviso that the total value of c for Fe is less than 0.5.

3. A process for the catalytic oxydehydrogenation of ethane to ethylene exothermically in the gas phase at a temperature of 550° C. or less by contacting the ethane under such conditions with a calcined catalyst comprising Mo, V, Nb and one additional element of the group Cu, Ce, Mn and U.

4. A process as in claim 3 in which the said catalyst contains the elements Mo, V, and Nb and Mn in the ratio:

$$Mo_dV_eNb_fMn_g$$

d is 16
e is 1 to 8
f is 0.2 to 10
g is 0.1 to 5

5. A process for the catalytic oxydehydrogenation of ethane to ethylene exothermically in the gas phase at a temperature of 550° C. or less by contacting the ethane under such conditions with a calcined catalyst comprising Mo, V, Nb and K.

6. A process as in claim 1 in which X comprises V, Nb and Mn.

7. A process as in claim 1 in which X comprises W and V.

8. A process as in claim 1 in which said calcined composition comprises the elements Mo, V and Mn.

9. A process as in claim 1 in which said calcined composition comprises the elements Mo, V, Nb and Ce.

10. A process as in claim 1 in which said calcined composition comprises the elements Mo, V, Nb and Cu.

11. A process as in claim 1 in which said calcined composition comprises the elements Mo, V, Nb and Mn.

12. A process as in claim 1 in which said calcined composition comprises the elements Mo, V, Nb and U.

13. A process as in claim 3 in which said catalyst comprises the elements Mo, V, Nb, and Ce.

14. A process as in claim 3 in which said catalyst comprises the elements Mo, V, Nb and Cu.

15. A process as in claim 3 in which said catalyst comprises the elements Mo, V, Nb and U.

16. A process as in claim 3 in which said catalyst comprises the elements Mo, V, Nb and Mn.

* * * * *

UNITED STATES PATENT AND TRADEMARK OFFICE
CERTIFICATE OF CORRECTION

PATENT NO. : 4,250,346

DATED : February 10, 1981

INVENTOR(S) : Frank G. Young et al.

It is certified that error appears in the above—identified patent and that said Letters Patent is hereby corrected as shown below:

In the abstract, line 14 of the Patent Grant, delete "and" in its first occurrence.

Col. 1, line 56 "831,322" should read --821,322--.

Col. 5, line 68 "those" should read --these--.

Col. 7, line 31 delete "b" before "3.4".

Col. 8, line 10 "positions" should read --positioned--.

Col. 9, line 12 "7/20$_2$" should read --7/2 O$_2$--.

Col. 9, line 23 "Space Velocity h$^{31}$ $^1$" should read --Space Velocity h$^{-1}$--.

Col. 9, line 43 "ygehydrogenating" should read --ydehydrogenating--.

Col. 9, line 48 "reporte" should read --reported--.

Col. 10, line 39 "avaporating" should read --evaporating--.

Col. 12, line 9 "ma" should read -- man- --.

Col. 14, line 20 "Fe(NO$_3$)$_3$·9H$_2$O(0.15" should read --"Fe(NO$_3$)$_3$·9H$_2$O(15--.

Col. 18, line 42 "K$_{0.06}$" should read --K$_{0.006}$--.

UNITED STATES PATENT AND TRADEMARK OFFICE
CERTIFICATE OF CORRECTION

PATENT NO. : 4,250,346
DATED : February 10, 1981
INVENTOR(S) : Frank G. Young et al.

It is certified that error appears in the above—identified patent and that said Letters Patent is hereby corrected as shown below:

Col. 22, line 2 "[$(NH_4)_2C_2O_4 \cdot H_2O$]" should read --[$(NH_4)_2C_2O_4 \cdot H_2O$]--.

Col. 22, line 25 "($Fe_2[SO_4]_3 \cdot 9H_2O$)" should read --($Fe_2[SO_4]_3 \cdot 9H_2O$)--.

Col. 26, line 4 "($SnCl_2 \cdot 2H_2O$)" should read --($SnCl_2 \cdot 2H_2O$)--.

Col. 29, line 28 "[$Co(CH_3COO)_2 \cdot 4H_2O$]" should read should read -- [$Co(CH_3COO)_2 \cdot 4H_2O$]--.

Col. 29, line 54 "[$Cr(C_2H_3O_2)_3 \cdot H_2O$]" should read --[$Cr(C_2H_3O_2)_3 \cdot H_2O$]--.

Col. 30, line 12 "[$(CH_3COO)_2Cu \cdot H_2O$]" should read --[$(CH_3COO)_2Cu \cdot H_2O$]--.

Col. 31, line 21 "($Ni(C_2H_3O_2)_2 \cdot 4H_2O$)" should read -- $Ni(C_2H_3O_2)_2 \cdot 4H_2O$)--.

UNITED STATES PATENT AND TRADEMARK OFFICE
CERTIFICATE OF CORRECTION

PATENT NO. : 4,250,346
DATED : February 10, 1981
INVENTOR(S) : Frank G. Young et al.

It is certified that error appears in the above-identified patent and that said Letters Patent is hereby corrected as shown below:

Col. 31, last line "$[(CH_3COO)_2UO_2.2H_2O]$" should read --$[(CH_3COO)_2UO_2 \cdot 2H_2O]$--.

Signed and Sealed this

Ninth Day of June 1981

[SEAL]

Attest:

RENE D. TEGTMEYER

Attesting Officer     Acting Commissioner of Patents and Trademarks